United States Patent [19]

Lee et al.

[11] Patent Number: 5,593,855

[45] Date of Patent: Jan. 14, 1997

[54] METHOD OF USING YEAST TO RECOVER PHYTIN BY PRECIPITATION FROM CORNSTEEP LIQUOR OR LIGHT STEEP WATER

[75] Inventors: Youl-Lark Lee; Sang-Jae Park, both of Seoul, Rep. of Korea

[73] Assignee: Doosan Technical Center, Kyunggi-do, Rep. of Korea

[21] Appl. No.: 417,137

[22] Filed: Apr. 4, 1995

Related U.S. Application Data

[63] Continuation-in-part of Ser. No. 149,972, Nov. 10, 1993, abandoned.

[30] Foreign Application Priority Data

Dec. 8, 1992 [KR] Rep. of Korea ............... 92-23622

[51] Int. Cl.⁶ ............................................. C12P 1/00
[52] U.S. Cl. ................. 435/41; 435/255.21; 435/255.4; 435/255.7
[58] Field of Search ....................... 435/41, 255.21, 435/255.4, 255.7

[56] References Cited

U.S. PATENT DOCUMENTS

| | | | |
|---|---|---|---|
| 3,591,665 | 7/1971 | Kimura et al. | 260/983 |
| 4,163,010 | 7/1979 | Garbutt | 260/122 R |
| 4,303,680 | 12/1981 | Tanekawa et al. | 426/60 |
| 4,668,813 | 5/1987 | Ogawa et al. | 558/147 |
| 4,914,029 | 4/1990 | Caransa et al. | 435/101 |
| 5,064,762 | 11/1991 | Rabinowitz | 435/155 |

FOREIGN PATENT DOCUMENTS

| | | |
|---|---|---|
| 8602238 | of 0000 | China . |
| 4635075 | of 0000 | Japan . |
| 4626346 | of 0000 | Japan . |
| 4633958 | of 0000 | Japan . |
| 4217268 | of 0000 | Japan . |
| 6156142 | of 0000 | Japan . |
| 4316978 | of 0000 | Japan . |
| 6150989 | of 0000 | Japan . |

OTHER PUBLICATIONS

Howson et al, Enzyme Microb. Technol., 5:377–382, (1983).

Erdman Jr. JW, J. Am. Oil Chemists' Society 56: 736–741 (1971).

*Primary Examiner*—Marian C. Knode
*Assistant Examiner*—S. Saucier
*Attorney, Agent, or Firm*—Abelman, Frayne and Schwab

[57] ABSTRACT

A process for recovery of phytin with a higher purity comprises the steps of preparing LSW or CSL, inoculating a yeast into LSW or CSL, culturing the yeast therein to precipitate phytin and separating phytin by sedimentation. The method may comprise a further step of adding salt into CSL to accelerate the formation of phytin precipitate and increase the yield of phytin.

6 Claims, 3 Drawing Sheets

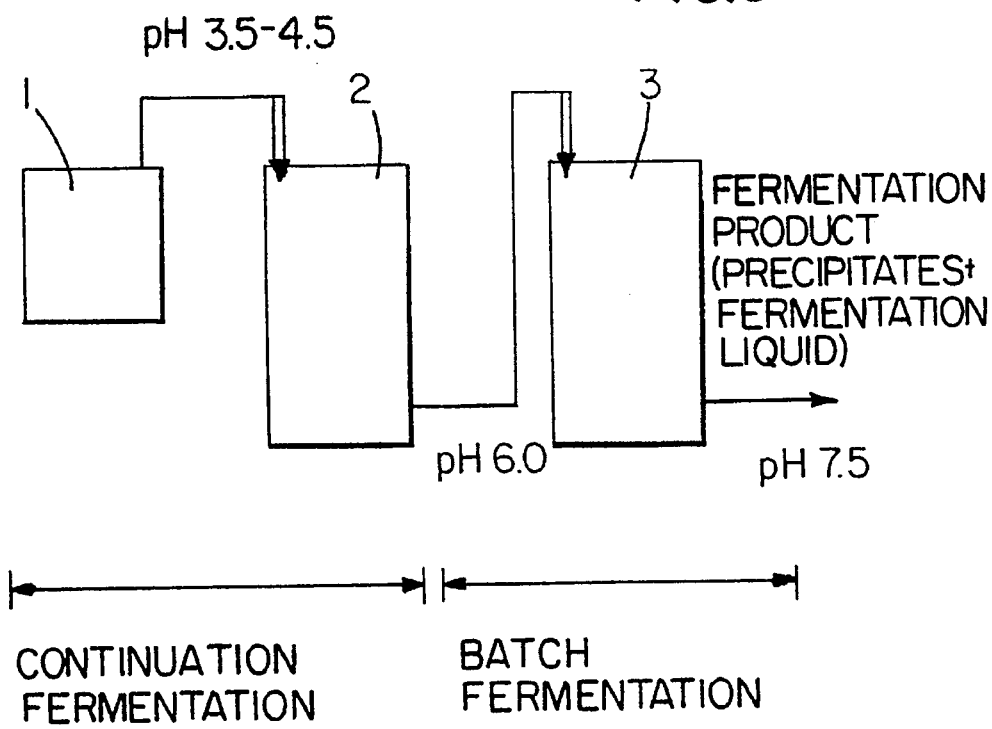
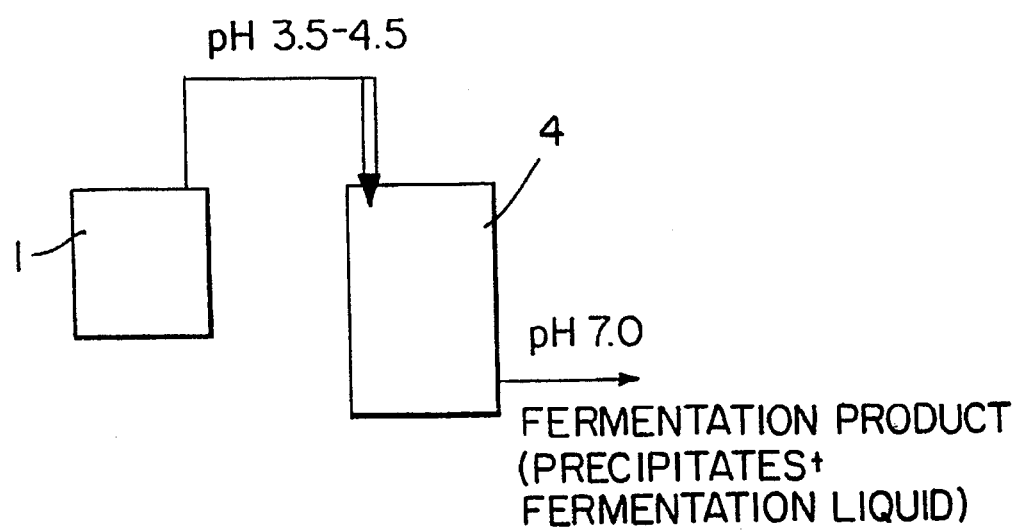

METHOD OF USING YEAST TO RECOVER PHYTIN BY PRECIPITATION FROM CORNSTEEP LIQUOR OR LIGHT STEEP WATER

BACKGROUND OF THE INVENTION

Field of the Invention

This application is a continuation-in-part of application Ser. No. 08/149,972, filed Nov. 10, 1993, now abandoned.

The present invention relates to a novel process for recovery of phytin with a high degree of purity and easy separation by sedimentation, characterized by inoculating and culturing a yeast in light steep water of corn (hereinafter, "LSW") or corn steep liquor(hereinafter, "CSL").

Description of the Prior Art

As known well to those skilled in this art, phytin, which is a metallic salt of inositol hexakisphosphatic acid, such as calcium phytate, magnesium phytate, zinc phytate, sodium phytate and the like, and means calcium or magnesium phytate especially, is distributed in almost all parts of plant tissue. Particularly, there exists a quantity of phytin in seeds. Phytin is known to be a storage material for phosphate in plants, so that it plays an important role in sprouting seeds and growing sprouts. For example, under course of sprouting seeds, phytins are decomposed by phytases to be used as a component of membrane or for a phosphorylation. Generally, phytin, which is water-insoluble and oderless white powder, is highly soluble in a weak acid of pH 2 to 3. From an economical view of industry, phytin is an important source for inositol and phytic acid, both of which are used in food industry.

Recently, in Japanese Patent Publication No. Sho. 43-16978 has been disclosed a method for producing water-soluble phytin that comprises varying the composition of metals in phytin. Under the condition of a high pressure and a high temperature, phytin is hydrolysed into inositol, which is also called mesoinositol or myoinositol. Inositol is contained in plants as well as found in the free state in such animal tissue as muscle, heart, liver and the like. In addition, inositol is also a component of phosphoglycerides which result from the esterification of phosphatidate and alcohol, such as serine, ethanolamine, choline, glycerol and inositol and are major kinds of membrane. As major components of membrane, the phosphoglycerides derived from phosphatidate and the above-mentioned common alcohol moieties are widely distributed in natural organisms, especially in mammalian liver and brain, egg yoke, soybean and white germ. Furthermore, inositol acts as a vitamin in higher animals and plays a role in the biosynthesis of fats and cholesterol. Therefore, inositol has recently come to be a health food.

In the meanwhile, phytic acid, which is such one that metals are removed from phytin, is a light brown or light yellow liquid in a syrup phase. It is dissolved well in a polar solvent such as water, 95% ethanol, acetone and the like, and is utilized for performing various, important roles. For example, it may be used as a component of a medicinal and fermentative composition, an agent for preventing blackish brown-coloration in canned provisions, an antioxidant, a softener for water, a corrosion inhibitor for metals, an agent for forming a metallic film, an additive for dye, an agent for concentrating rare earth elements, a solvent for polymers, and an anti-explosive agent for liquid fuel such as gasoline, kerosine and the like.

Conventionally, phytin is recovered by adding alkali such as potassium hydroxide and sodium hydroxide into corn steep liquor, light steep water or rice bran to adjust the pH of the substrate into 7.0 to 8.0 and thence, to precipitate phytin. This type of the processes is described in Japanese Patent Publication Nos. Sho. 46-35075, 46-26346, 46-33958 and 42-17268, and U.S. Pat. Nos. 3,591,665 and 4,163,010.

Methods for the production of phytic acid are disclosed in U.S. Pat. No. 4,668,813, Japanese Pat. Laid-Open No. Sho. 61-056142 and Chinese Pat. Laid-Open No. 8602238, in which a phytin-containing solution such as CSL, acid extract of rice bran and the like is treated with an anion exchange resin with phytin adsorption to recover phytin which is then subjected to the treatment of desalting to prepare phytic acid. In addition, Japanese Patent Laid-Open No. Sho. 61-050989 describes a method for producing phytic acid in which a further step of ultrafiltration is comprised.

However, the above-mentioned techniques have several problems in practical performance. For example, in case of the production of phytin by adjusting pH, that is, neutralization, the viscosity of phytin-containing solution rises, so that it is not easy to separate the precipitate. On the other hand, in case of using an anion exchange resin column, the process requires several steps to separate the phytate and the production cost of phytin becomes increased.

SUMMARY OF THE INVENTION

For solving the aforementioned problems, the present inventors have recognized that there exists a need for a process to separate phytin precipitates easily and economically, and have made use of such a principle that culturing a yeast in LSW or CSL causes phytin to precipitate by the increase of the pH of the substrate, as the content of lactic acid as a carbon source decreases.

Accordingly, in an aspect of the present invention, there is provided a method for recovery of phytin with a high degree of purity by cultivation of a yeast in CSL or LSW and by sedimentation of phytin precipitates.

In accordance with the present invention, the method for recovery of phytin comprises the steps of preparing LSW or CSL, inoculating a yeast selected from the group consisting of *Saccharomyces cerevisiae, Saccaromyces uvarum, Saccharomyces awamori, Saccaromyces diastacticus, Candida albicans, Candida lustaniae* and *Kluyveromyces lactis*, into the light steep water or the corn steep liquor, culturing the yeast therein to precipitate phytin and separating phytin by sedimentation. The method may comprise a further step of adding salts into the diluted CSL to accelerate the formation of the precipitate and to increase the yield of precipitate.

BRIEF DESCRIPTION OF THE DRAWINGS

The above and other object, features and advantages of the present invention will be more apparent from the following detailed description taken with reference to the accompanying drawings, in which:

FIG. 3 is a schematic, flow sheet illustrating a system of semi-continuous culture for performing the process according to the present invention; and FIG. 4 is a schematic, flow sheet illustrating a system of continuous culture for performing the process according to the present invention.

Figure 1:
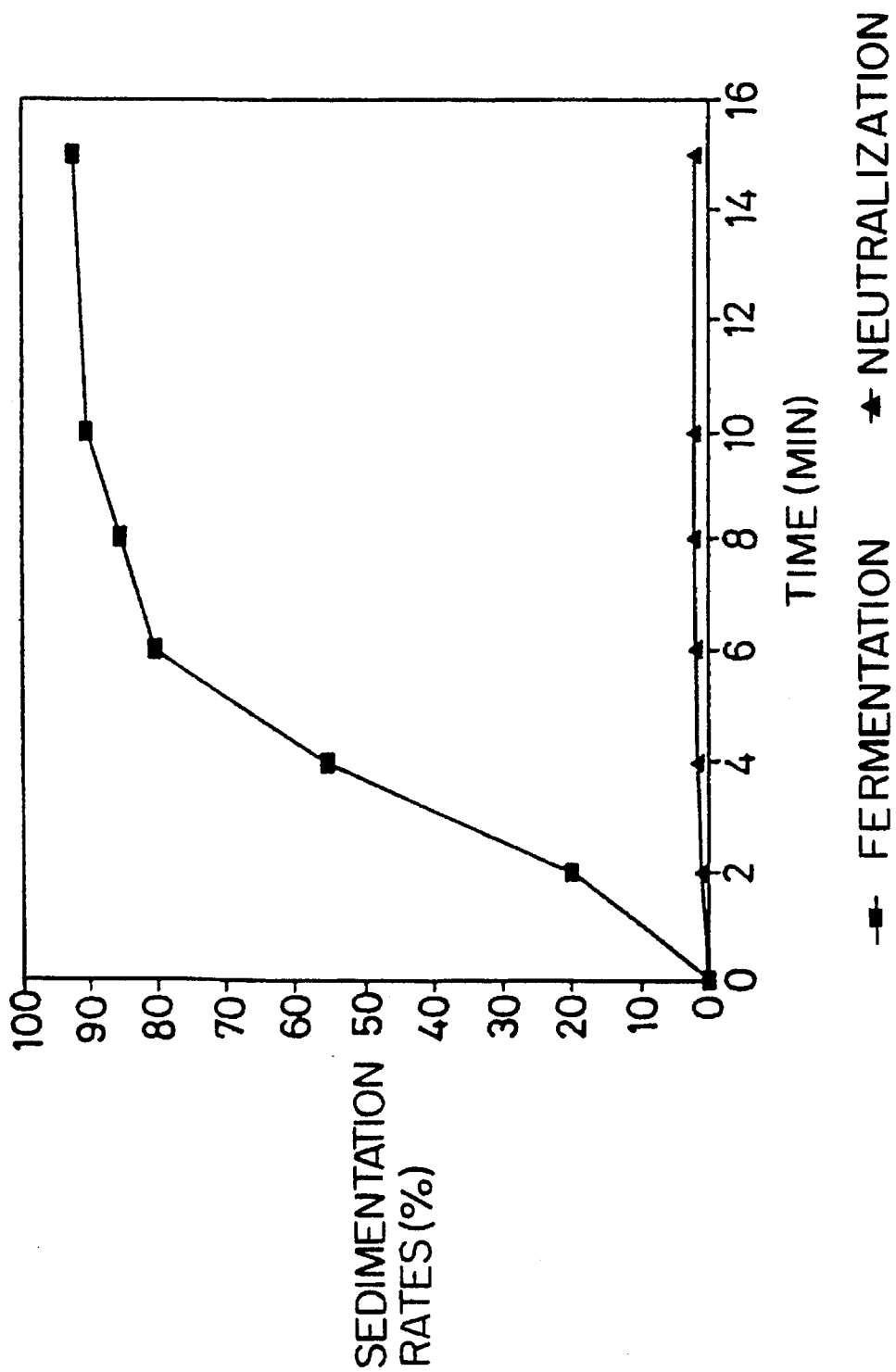
FIG. 1 is a graph illustrating the sedimentation rates of the phytin recovered according to the present invention and by a conventional neutralization method, in which and represent the rates by the present invention and the conventional method, respectively.

To the accomplishment of the foregoing and related objects, this invention, then, comprises the features of improvement hereafter fully described in the specification and particularly pointed out in the claims, the following description and the accompanying drawing setting forth in detail a certain illustrative embodiment of the invention, this being indicative, however, of but one of the various ways in which the principles of the invention may be employed.

DETAILED DESCRIPTION OF THE INVENTION

In accordance with the present invention, as a medium for yeast, LSW of 5 to 13% solid content with an initial pH of 3.5 to 4.5, or CSL of 5 to 20% solid content diluted with water from 40 to 55% solid content is prepared. The unit % solid indicates solid weight/100 ml LSD or CSL.

The yeasts for the production of phytin in the present invention are those cultured previously in a liquid medium for 1 day. The liquid medium, which is conventional one, is for example, either a YPD medium consisting of 1% by weight per volume (hereinafter "w/v") of yeast extract, 5% (w/v) of glucose and 1% (w/v) of peptone, or LSW of 5 to 13% solid. The pre-cultured yeasts are inoculated into the LSW or CSL to be cultured at 20° to 40° C. for 1 to 4 day(s). The volume of the inoculation is preferably on the order of 1 to 20% (v/v), as based on LSW or CSL volume. Generally, among fungi except for Phycomycetes, there are a few groups that have largely lost a mycelium habit of growth and have become unicellular. Such organisms are known collectively as yeast. A typical yeast consists of small, oval cells that multiply by forming buds. Generally yeasts do not live in soil but instead have adapted themselves to environments with a high sugar content, such as the nectar of flowers and the surface of fruits. Many yeasts (the fermentative yeasts) perform an alcoholic fermentation and thus have been long exploited to make wine and bread. Yeasts are classified in all three classes of higher fungi: Ascomycetes, Basidiomycetes, and Fungi Imperfecti. Among these yeasts, any one that is capable of utilizing lactic acid as a carbon source may be used to recover phytin in accordance with the present invention. But the yeast that produces phytase is unavailable in the present invention, since it can not utilize lactic acid as a carbon source to precepitate phytin and phytase secreted by yeast decomposes phytate to inositol and phosphate, not to form a precipitate of phytin. Therefore, for example, there may be used *Saccharomyces sp.* such as *Saccharomyces cerevisiae, Saccharomyces uvarum, Saccharomyces awamori* and *Saccharomyces diastaticus, Candida sp.* such as *Candida albicans* and *Candida lusitaniae, Kluyveromyces sp.* such as *Kluyveromyces lactis*, and the like. The above-mentioned yeast species are only indicative, but not limitative.

An agitation culture with a rotation rate of 100 to 500 rpm is adapted. After culturing yeasts, the final pH of the LSW and the dilute CSL are in the range of 6.0 to 8.5 and 5 to 8, respectively. When the pH of the LSW is more than 6.0 and that of the CSL is more than 5.0, phytin starts to precipitate. As the pH of LSW or CSL increases, the precipitate of phytin becomes slowly formed with the same rate as that of pH rising. The sedimentation rate of the precipitate in the present invention is higher than that in the conventional method, since the precipitate is slowly formed for a long period and thus its size becomes larger. Accordingly, it is also easy to separate from the supernatant. The generation of the precipitate and the growth of the yeast are irrelevant to whether the medium is sterilized or not.

The fermentation process for recovering phytin according to the present invention may further comprise the addition of metallic salts, for example, calcium salt such as calcium chloride and calcium hydroxide, and magnesium salt such as magnesium hydroxide carbonate and magnesium chloride into the dilute CSL so as to increase the amount of the precipitate. When an anion is added to the CSL, it does not affect the formation of phytin precipitate. Rather, it decreases the pH and may prohibit the formation of phytin precipitate. Such cation can only increase the amount of the precipitate. In case of the dilute CSL, the amount of precipitates formed by only culturing yeasts is very small. However, the addition of the above-mentioned salts may increase the amount of the precipitate remarkably, and the precipitate shows an excellent sedimentation property so that it can be easily separated from the supernatant. The amount of the salt added to the dilute CSL is preferably on the order of about 0.01 to 2.0% (w/v). For example, if too small the amount is used, the effect of the salt is not expressed. On the other hand, if too large the amount is used, the pH of the medium becomes too much increased and thus it causes the same problems as in the conventional neutralization method. In the meantime, in case of the LSW, the addition of the salts does not have a great influence on the sedimentation property and the purity of the precipitate. The LSW inherently comprises a divalent cation such as $Ca^{2+}$, $Mg^{2+}$, and $Zn^{2+}$, especially $Mg^{2+}$, and said ion has a great influence on the formation of phytin precipitate. However, in case of the CSL, when it is concentrated, such cation is removed as a precipitate by the combination of said cation and an anion like $SO_4^{2-}$. Thus the concentration of said cation in the CSL is too low to form a desired amount of phytin precipitate. The addition of the salts to the LSW makes the precipitate put on a brownish color.

Phytic acid and inositol may be prepared conventionally from the phytin recovered by the method according to the present invention. For example, the phytin is subjected to the treatment of desalting, purifying, etc. to prepare phytic acid. The phytic acid can be further treated to prepare inositol using any known treatment such as hydrolysis under pressure, separation of phosphates, and purification.

Referring now in detail to the drawings, wherein like reference numerals designate like parts in a few figures, and initially to FIG. 1, a graph illustrates the comparison of the sedimentation rates according to a conventional neutralization method and the present fermentation method. The sedimentation rates are measured by putting each of medium solutions containing the produced precipitates by the above neutralization and fermentation methods in a 50 ml mass cylinder. As shown in FIG. 1, the phytin produced by the fermentation method according to the present invention is precipitated completely with in 10 minutes, whereas that produced by the conventional neutralization method does not at all. Therefore, it is found that the present fermentation method is more preferable than the conventional neutralization method in view of separation of phytin.

Figure 2:
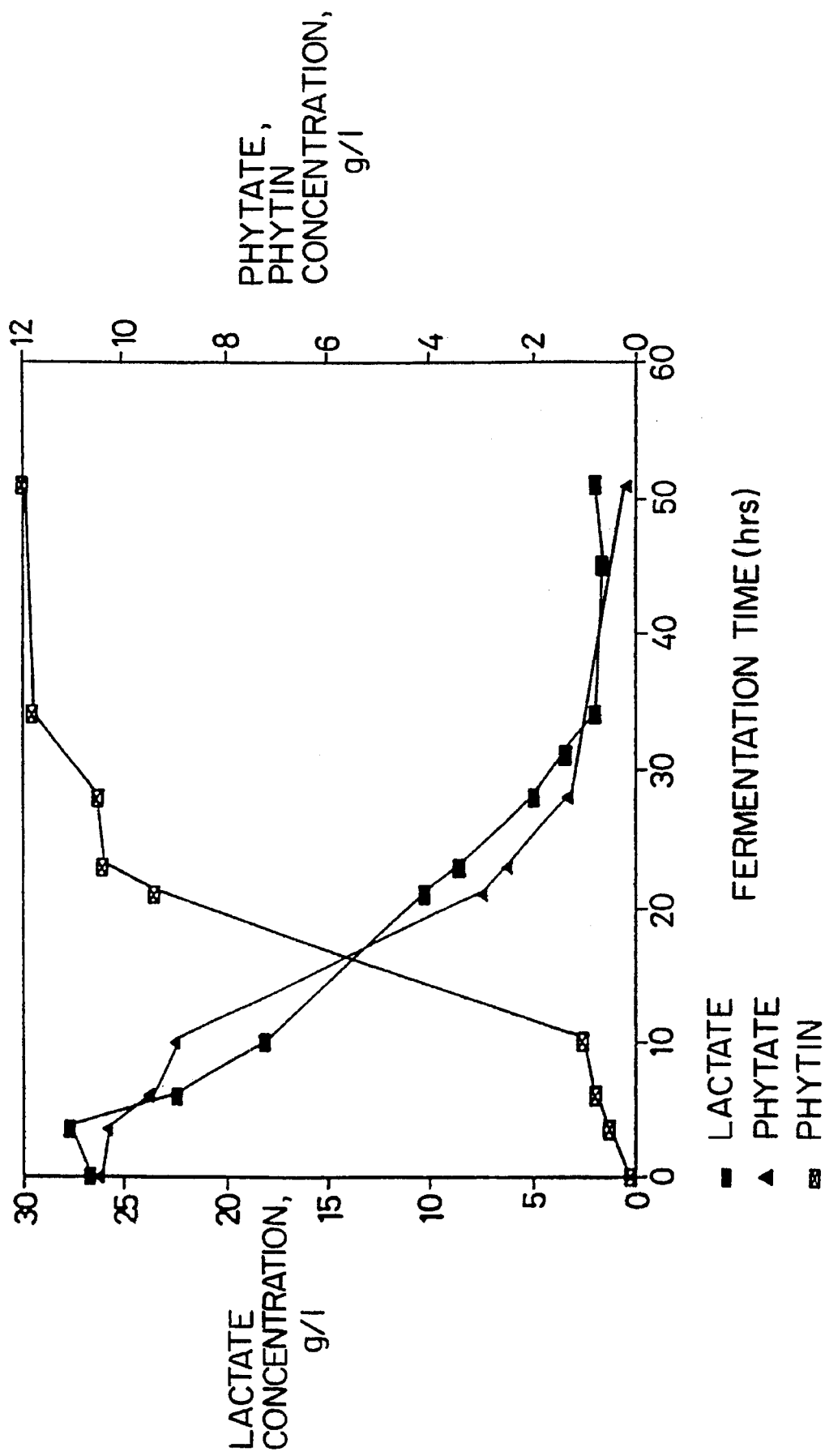
FIG. 2 is a graph illustrating the profiles of lactate and phytate concentration during fermentation and the profile of phytin precipitates formed during fermentation according to the present invention.

FIG. 2 is a graph illustrating the profiles of lactate and phytate concentration during fermentation and the profile of phytin precipitates formed during fermentation according to the present invention. As shown in FIG. 2, as the yeast consumes the lactic acid contained in the LSW or CSL as a carbon source during fermentation, the pH increase caused by yeast fermentation makes phytates precipitate. Because lactic acid which makes the viscosity increase is removed by said fermentation, even if the LSW is concentrated more than 50% solid content, the increase of viscosity thereof becomes relieved largely enough to raise the degree of concentration. In addition, when the concentrated medium prepared by fermentation is added to and is applied for feedstuff, the feedstuffs may be further concentrated easily and a degree of concentration may become much more increased. Furthermore, there are obtained such concomitant effects that the added yeasts contribute to nutritive qualities, remove a sour taste from the feedstuffs, and thus, increase the quality of the feedstuffs.

FIG. 3 illustrates schematically a processing system of semi-continuous culture performing the fermentation method according to the present invention. As shown in FIG. 3, a reservoir 1 of CSL or LSW having a pH of 3.5 to 4.5 is connected to a primary fermenter 2, a partial growth chamber, to continuously supply fresh medium. In the primary fermenter 2, the growth of the yeasts is initiated, that is, the yeast is inoculated. The yeasts become to partially grow until the pH of the medium containing the microorganisms is, for example, 6.0. Subsequently, the partially fermented medium is transferred to a secondary fermenter 3, which is a system of batch culture, to perform the last fermentation of the medium up until, for example, pH 7.5. After finishing the fermentation, the fermented product is drained to be separated into precipitates and supernatant.

FIG. 4 illustrates schematically a processing system of continuous culture performing the fermentation method according to the present invention. As shown in FIG. 4, the reservoir 1 of CSL or LSW with a pH of 3.5 to 4.5 is connected to a fermenter 4, a growth chamber. Once growth has been initiated, fresh medium is continuously supplied from the reservoir 1. The volume of medium in the fermenter is maintained to be constant by allowing the excess volume to be removed continuously through, for example, a siphon overflow with a pH of, for example, 7.0. Then, the overflow is separated into precipitates and supernatant.

Of course, the process according to the present invention may be performed in a system consisting of only batch culture, such as flask culture in which nutrients are not renewed and hence growth remains exponential for only a few generations.

The semi-continuous culture and the continuous culture allow phytin to be obtained in the yields of 1.2% and 0.85%, respectively.

In accordance with the present invention, the precipitate, after performing the fermentation, may be yielded in the rates of 1 to 2.5% (w/v) in the LSW and 1 to 3% (w/v) in the dilute CSL, which are correspondent to the level of about 85 to 100% in the conventional neutralization.

After performing the fermentation, the fermented solution is transferred to a separatory funnel and then, left for 10 minutes to separate the precipitate, which is subsequently washed with distilled water and dried. A phytate analysis for the precipitate, which comprises the dissolution of the precipitates in acid, shows such a result that the purity of the precipitate produced by the present fermentation is on the order of from about 60 to about 95%, which is higher than that of the precipitate produced by the conventional neutralization. With regard to the CSL, the precipitate produced by fermenting the yeasts in combination with adding the salts such as calcium carbonate has a high purity of, for example, at least 90%, which is much higher than conventional one (70%) by the neutralization when it is analyzed by a method according to Ali I. Mohamed in Cereal Chem. 63(6), 475–478, 1986.

EXAMPLE 1

100 ml of LSW having 9.2% solid was filled in a 500 ml baffle flask, into which 5 ml of a solution already inoculated with *Saccharomyces uvarum* NRRL Y-236 was added to be cultured therein. The inoculated flask was agitated in a rate of 250 to 350 rpm at 30° C. When the pH of the cultured medium was finally reached to above 7.5, it was poured into a separatory funnel and left for 10 minutes to separate precipitates. The separated precipitates were provided with 100 ml of distilled water and agitated, well. Thereafter, this mixture was poured again into another separatory funnel to sink the precipitates, which were then separated and dried in a drying oven at 100° C. to obtain phytin. Measurement and analysis were performed. The results were that weight is 1.03 g and purity is 85%.

To know the ratios of metallic ions contained in the precipitates, the precipitates were dissolved in acid and analyzed with an atomic absorption spectroscope. Their results are given as shown in Table 1.

EXAMPLE 2

100 ml of LSW of 9.2% solid in combination with 0.5 g of anhydrous $CaCO_3$ was filled in a 500 ml baffle flask, into which 5 ml of a solution already inoculated with *Saccharomyces cerevisiae* LA was added to be cultured therein. The inoculated flask was agitated in a rate of 250 to 350 rpm at 30° C. When the pH of the cultured medium was finally reached to above 7.5, it was poured into a separatory funnel and left for 10 minutes to separate precipitates. The separated precipitates were provided with 100 ml of distilled water and agitated, well. Thereafter, this mixture was poured again into another separatory funnel to sink the precipitates, which were then separated and dried in a drying oven at 100° C. to obtain 1.30 g of phytin. Purity. 79%. The ratios of metallic ions contained in the precipitates are given as shown in Table 1.

EXAMPLE 3

CSL of 52% solid was diluted with distilled water into CSL of 12% solid and added into a 500 ml baffle flask. 0.5 g of $CaCl_2 \cdot 2H_2O$ was dissolved in the diluted CSL, into which 5 ml of a solution already inoculated with *Kluyveromyces lactis* ATCC 56498 was added to be cultured therein. The inoculated flask was agitated in a rate of 250 to 350 rpm at 30° C. for 2 days. When the pH of the cultured medium was finally reached to 5.9, it was poured into a separatory funnel and left for 10 minutes to separate precipitates. The separated precipitates were provided with 100 ml of distilled water and agitated well. Thereafter, this mixture was poured again into another separatory funnel to sink the precipitates, which were then separated and dried in a drying oven at 100° C. to obtain 0.58 g of phytin. Purity. 79%. The ratios of metallic ions contained in the precipitates are given as shown in Table 1.

EXAMPLE 4

CSL of 52% solid was diluted with distilled water into CSL of 10% solid and 100 ml was poured into a 500 ml baffle flask. Precipitates were produced in a manner similar to Example 3 except that $CaCl_2 \cdot 2H_2O$ is not used. The precipitates were separated in a drying oven at 100° C. to obtain 0.49 g of phytin. Purity. 88%. The ratios of metallic ions contained in the precipitates are given as shown in Table 1.

EXAMPLE 5

Precipitates were produced in a manner similar to Example 3 except that CaCO3, *Kluyveromyces lactis* ATCC 56489, and the pH 6.40 were substituted for $CaCl_2 \cdot 2H_2O$, *Saccharomyces cerevisiae* and pH 5.9, respectively. 1.04 g of phytin was obtained. Purity 95%.

The ratios of metallic ions contained in the precipitates are given as shown in Table 1.

EXAMPLE 6

1 l of LSW having a concentration of 9.2% solid was poured into a 3 l primary fermenter, into which *Candida lusitaniae* ATCC 34449 was then inoculated. A reservoir containing LSW of 9.2% solid was connected to the primary fermenter to continuously supply the fresh medium so as to stay in the primary fermenter for 15 hours. This partial fermented overflow was transferred into a secondary fermenter to perform a batch culture until the pH of the fermented medium is 7.5. After finishing the culture, the fermented product was drained to separate precipitates.

According to the above semi-continuous culture, 12 g of phytin per 1 l of LSW was obtained. Purity 82%.

The ratios of metallic ions contained in the precipitates are given as shown in Table 1.

EXAMPLE 7

1 l of LSW having a concentration of 9.2% solid was poured into a 3 l fermenter, into which *Saccharomyces diastacticus* ATCC 13007 was then inoculated to be cultured for 30 hours. When the pH of the medium reached 7.0, a reservoir containing LSW of 9.2% solid was connected to the fermenter to supply fresh medium in a rate of 0.1/l hour. The volume of medium in the fermenter was maintained constant by allowing the excess volume to be removed in the same rate. Then, the overflow was separated into precipitates and aqueous liquid.

According to this continuous culture (dilution rate=0.1 hour), 12 g of phytin per 1 l of the LSW medium were yielded. Purity 80%.

The ratios of metallic ions contained in the precipitates are given as shown in Table 1.

COMPARATIVE EXAMPLE 1

100 ml of LSW of 9.2% solid were titrated with calcium hydroxide of 5% (w/v) so as to have pH 7.0. The titrated LSW was filtered, washed with distilled water and dried in a drying oven at 105° C. for 3 hours to obtain 1.5 g of precipitates.

The ratios of metallic ions contained in the precipitates are given as shown in Table 1.

COMPARATIVE EXAMPLE 2

3.5 g of precipitates was obtained in a manner similar to Comparative Example 1 except that 50 ml of CSL of 52% solid were used instead of 100 ml of the LSW of 9.2% solid. The ratios of metallic ions contained in the precipitate are given as shown in Table 1.

As shown in Examples 1 and 2, in case of the LSW, the addition of calcium salt does not have a great influence on the purity of the precipitate. As shown in Examples 3 and 4, in case of the CSL, the addition of the salts such as calcium salt increases the yield of precipitates.

TABLE 1

The ratios of metal ion contained in the precipitates.

| Exam. No. | Ca(%) | Na(%) | Mg(%) | Zn(%) | Total |
|---|---|---|---|---|---|
| 1 | 5.11 | 0.51 | 93.28 | 1.10 | 100% |
| 2 | 80.35 | 1.37 | 18.44 | 0.84 | 100% |
| 3 | 94.52 | 0.34 | 4.14 | 1.00 | 100% |
| 4 | 8.2 | 0.5 | 90.3 | 1.00 | 100% |
| 5 | 93.67 | 0.50 | 3.88 | 1.95 | 100% |
| 6 | 5.00 | 0.62 | 94.30 | 0.08 | 100% |
| 7 | 5.1 | 0.54 | 94.20 | 0.16 | 100% |
| C.1 | 89.21 | 0.31 | 9.56 | 0.92 | 100% |
| C.2 | 93.11 | 0.85 | 5.25 | 0.79 | 100% |

As indicated in the above Table 1 by the analysis of the precipitate from Examples and Comparative Examples, the metal composition of precipitate according to the present fermentation (Examples 2, 3, and 5) is similar to that of precipitate according to the conventional neutralization, namely, in case of the fermentation in combination with adding calcium salt in a concentration of 0.5%, the precipitate has a remarkably increased concentration of the calcium ion. But the sedimentation rate according to the present invention(Example 1) is considerably higher than that according to the conventional method(Comparative Example 2) in view of recovery rate of phytin, as shown in FIG. 1.

From the Examples and the Comparative Examples, the phytin produced by the process according to the present invention has an excellent sedimentation rate and thence may be easily separated. In addition, the process according to the present invention is capable of producing phytin having a high purity. Since the LSW in which phytin and lactate are removed by the present fermentation, causes lower viscosity increase during concentration, a degree of concentration become much more increased. When the concentrated medium comprising yeast is applied for feedstuff, the nutritive qualities are improved.

What is claimed is:

1. A process for the recovery of phytin consisting essentially of the steps of:

preparing light steep water of 5 to 13% solid content or corn steep liquor of 5 to 20% solid content;

inoculating a yeast selected from the group consisting of *Saccharomyces cerevisiae, Saccharomyces uvarum, Saccharomyces awamori, Saccharomyces diastaticus, Candida albicans, Candida lusitaniae* and *Kluyveromyces lactis* into the light steep water or corn steep liquor;

culturing the yeast therein under conditions to precipitate phytin;

and separating the precipitated phytin by sedimentation.

2. The process according to claim 1 wherein the corn steep liquor further comprises a magnesium salt in a concentration of about 0.01 to about 2.0%.

3. The process according to claim 2 wherein the magnesium salt is selected from the group consisting of magnesium carbonate and magnesium chloride.

4. The process according to claim 1 wherein the corn steep liquor further comprises a calcium salt in a concentration of about 0.01 to about 2.0%.

5. The process according to claim 4 wherein the calcium salt is selected from the group consisting of calcium carbonate, calcium chloride and calcium hydroxide.

6. The process according to claim 1 wherein the light steep water or corn steep liquor contains lactic acid.

* * * * *